United States Patent
Reza et al.

(10) Patent No.: US 12,233,048 B2
(45) Date of Patent: Feb. 25, 2025

(54) SUSTAINED RELEASE MELATONIN COMPOSITIONS

(71) Applicant: Société des Produits Nestlé S.A., Vevey (CH)

(72) Inventors: Md Ehtesham Reza, Fair Lawn, NJ (US); Vesselin Danailov Miladinov, Denville, NJ (US); Richard Mark Warrington, Ridgewood, NJ (US)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 18/434,065

(22) Filed: Feb. 6, 2024

(65) Prior Publication Data

US 2024/0173294 A1 May 30, 2024

Related U.S. Application Data

(63) Continuation of application No. PCT/EP2023/078064, filed on Oct. 10, 2023.

(60) Provisional application No. 63/455,331, filed on Mar. 29, 2023, provisional application No. 63/416,074, filed on Oct. 14, 2022.

(51) Int. Cl.
| | |
|---|---|
| *A61K 31/4045* | (2006.01) |
| *A61K 9/00* | (2006.01) |
| *A61K 47/12* | (2006.01) |
| *A61K 47/26* | (2006.01) |
| *A61K 47/36* | (2006.01) |
| *A61K 47/46* | (2006.01) |

(52) U.S. Cl.
CPC ........ *A61K 31/4045* (2013.01); *A61K 9/0056* (2013.01); *A61K 47/12* (2013.01); *A61K 47/26* (2013.01); *A61K 47/36* (2013.01); *A61K 47/46* (2013.01)

(58) Field of Classification Search
None
See application file for complete search history.

(56) References Cited

U.S. PATENT DOCUMENTS

| | | | |
|---|---|---|---|
| 2012/0195968 A1* | 8/2012 | Shah | A61K 9/2054 514/415 |
| 2016/0243038 A1* | 8/2016 | Shah | A61K 31/7034 |
| 2019/0247312 A1* | 8/2019 | Cardona | A61P 39/06 |
| 2022/0287355 A1* | 9/2022 | Daniel | A24B 15/308 |

FOREIGN PATENT DOCUMENTS

| | | |
|---|---|---|
| CN | 114259490 | 4/2022 |
| WO | 2019/002657 | 1/2019 |
| WO | 2021/144403 | 7/2021 |
| WO | 2022/090977 | 5/2022 |
| WO | 2023/194899 | 10/2023 |

OTHER PUBLICATIONS

Written Opinion of the International Searching Authority for Application No. PCT/EP2023/078064 dated Jan. 22, 2024 (5 pages).
International Search Report for Applicaiton No. PCT/EP2023/078063 dated Jan. 22, 2024 (3 pages).

\* cited by examiner

*Primary Examiner* — Robert A Wax
*Assistant Examiner* — Quanglong N Truong
(74) *Attorney, Agent, or Firm* — K&L Gates LLP

(57) ABSTRACT

The present invention relates to a composition comprising melatonin encapsulated within a calcium alginate hydrogel. It further provides an orally administrable dosage form comprising such a composition held within a gel, wherein the gel is formed using starch as a gelling agent. Processes to produce these compositions, as well as their use in therapy, are also disclosed.

18 Claims, 2 Drawing Sheets

SUSTAINED RELEASE MELATONIN COMPOSITIONS

CROSS REFERENCE TO RELATED APPLICATIONS

The present application is a continuation of International Application No. PCT/EP2023/078064 filed Oct. 10, 2023, which claims priority to U.S. Provisional Appl. Ser. No. 63/455,331 filed Mar. 29, 2023 and U.S. Provisional Appl. Ser. No. 63/416,074 filed Oct. 14, 2022, the entire contents of which are incorporated herein by reference.

FIELD OF THE INVENTION

The present invention relates to a melatonin composition which is useful for the preparation of orally administrable gelatinised dosage forms which provide sustained release of melatonin upon consumption.

BACKGROUND OF THE INVENTION

Melatonin (N-acetyl-5-methoxytryptamine; CAS Number: 73-31-4; $C_{13}H_{16}N_2O_2$; molecular weight: 232.3) is the primary hormone secreted from the pineal gland in vertebrates. Endogenous melatonin is known to play a role in regulating sleep-wake cycle (circadian rhythm), pubertal development and seasonal adaption, with the mechanism of action well understood. Physiological levels of melatonin are approximately 10 pg/ml during the daytime, with levels increasing to approximately 100 pg/ml during the night time. Levels of melatonin have also been found to vary with age. The peak secretion of melatonin occurs at around 2 AM.

The therapeutic use of exogenous melatonin has also been well studied. R. J. Reiter et al., Curr. Med. Chem. 2010, 17(19), 2070-2095 reviewed the clinical use of melatonin in human trials. In particular, melatonin has found use as an adjuvant therapy for macular degeneration, glaucoma, protection of the gastric mucosa, irritable bowel syndrome, arterial hypertension, diabetes, side effects of chemotherapy and radiation in cancer patients or hemodialysis in patients with renal insufficiency and, especially, for sleep disorders of circadian etiology (jet lag, delayed sleep phase syndrome, sleep deterioration associated with aging, etc.) as well as in those related with neurological degenerative diseases (Alzheimer, etc.,) or Smith-Magenis syndrome. Melatonin has been used in doses ranging from 0.1 mg to 300 mg, and observed to have low toxicity, and is non-addictive.

The most notable therapeutic use of melatonin is for the treatment of sleep disorders. Melatonin has become one of the most frequently requested over-the-counter sleep aids, aiding with the duration of sleep and falling asleep more quickly. N. Covasin et al., JAMA. 2022, 327(5), 483-485 and coworkers report that the consumption of melatonin supplements have increased 5-fold from 1999-2000 (0.4%) to 2017-2018 (2.1%) among American adults (n=55021, mean age 47.5[SD 17.1] years; 52% women).

As a testament to its widespread use, a range of dosage forms of melatonin are available, which include liquid, tablet, capsule and gummy formulations. Exemplary gummy formulations include Natrol® 10 mg melatonin gummies, a nutraceutical to aid with falling asleep faster and staying asleep longer. Natrol® Melatonin Gummies are non-GMO, vegan and free of gluten, gelatin, artificial colors, flavors, sweeteners and preservatives. Similarly, Nature's Bounty® immediate release melatonin products include Sleep Gummies comprising 3 mg Melatonin and 200 mg L-Theanine per serving. Other ingredients include corn syrup, sugar, gelatin. citric acid, fractionated coconut oil (containing carnauba wax), natural flavor, pectin and vegetable and fruit juice (for colour).

However, despite the large number of available compositions, there remains a number of challenges with administering exogenous melatonin. Firstly, melatonin is documented to have poor and highly variable bioavailability. This is due to its short half-life of 20-50 minutes, and high first-pass metabolism in the liver, and/or poor gut absorption. Further, it can take more than 30 minutes after ingestion for the blood plasma concentration of melatonin to reach its peak. In some cases, melatonin has to be administered up to 2 hours before sleep. As a consequence, low dosages of 0.1-1 mg, which would correspond to physiological blood plasma level are much less effective than high dosages. However, high dosages are less desirable, at least because of the persistence of melatonin in the blood after waking, when the physiological levels should be very low.

To this end, solutions to solve the above problems have focused on innovative methods for a sustained release of melatonin throughout a night's sleep. This would maintain peak blood plasma concentration for a longer period of time, and therefore would lead to improved quality of sleep (such as reduced chances of waking up). For this reason, sustained release melatonin supplements are considered superior to immediate release supplements.

CIRCADIN® produced by Neurim Pharmaceuticals (disclosed in U.S. Pat. No. 6,469,044), is a 2 mg prolonged-release melatonin tablet for treating insomnia in patients over 55 years of age. The component responsible for the slow release profile is an acrylic resin carrier (EUDRAGIT® RS 100, Ammonio methacrylate copolymer type B), which decreases the rate of dissolution of melatonin. However, WO2018/078429 discloses issues of patient compliance with CIRCADIN® due to the difficulty in swallowing the large tablets (8.1 mm diameter and 3-5 mm thick). When Circadin® tablets are broken, crushed or chewed by the patient, they exhibit a release profile that is close to immediate-release melatonin.

SLYENTO® is indicated for the treatment of insomnia in children and adolescents aged 2-18 with Autism Spectrum Disorder (ASD) and/or Smith-Magenis syndrome. The tablets comprise 1 or 5 mg of melatonin, and similarly uses an acrylic resin carrier for the slow release profile (Ammonio methacrylate copolymer type A/B).

WO2020/150605 discloses tablet and capsule dosage forms comprising a solid micronized melatonin composition. The granules melatonin contain a carboxylic acid and a hydrogel-forming polymer, which upon ingestion impart a slow-release profile. However, the inventors report that the dosage form must be prepared by dry granulation, and wet methods should be avoided. This was due to water causing melatonin to deaminate, which reduces the content uniformity of the dosage form.

WO2012/103411 describes multi-layered slow-release melatonin tablets, wherein the slow-release layer comprises a material capable of forming a hydrogel.

Despite gummy formulations being a favoured dosage form of exogenous melatonin, research into sustained release gummies is limited. The primary reason for this is there are many greater challenges in the development of sustained release gummies over the corresponding tablets. For example, existing technologies for sustained release melatonin tablets depend on a layered structure, however, this approach is unsuitable for gummies. Furthermore, gummies are prepared at elevated temperatures using high shear forces, and these harsh conditions are detrimental to the stability of the sustained release form of melatonin.

To the best of our knowledge, there are only two prior disclosures of sustained release melatonin gummies. WO2021/144403 discloses a hydroxypropyl methylcellulose (HPMC) gummy formulation comprising melatonin pellets formed by spray-coating micronized melatonin dispersed in a 10% aqueous solution of HPMC onto microcrystalline cellulose (MCC) spheres. One limitation of this approach is that HPMC is a cellulose-based coating which is known to dissolve at about 65° C. Thus, these slow-release melatonin pellets are limited to a narrow set of gummy-manufacturing processes, given that the heating step in the preparation of a gummy can exceed 90° C. NiteThru® two-stage release gummies produced by Strides Consumer LLC comprise 6 mg of melatonin in two forms: one as an immediate release formulation, and also a slow-release encapsulated melatonin. Other ingredients include corn syrup, cane sugar, stevia, purified water, pectin, carrageenan, gellan gum, citric acid, sodium citrate, strawberry flavor, natural colour (E-163), carnuba wax, microcrystalline cellulose, polyvinyl acetate, basic methacrylate copolymer and stearic acid. However, there is growing concern with consumers that carrageenan, present in some gummy compositions, is harmful to human health.

Therefore, there remains a need to provide an improved sustained release melatonin gummy to maintain peak blood plasma concentration of melatonin for longer periods of time and therefore improve the quality of restful sleep.

SUMMARY OF THE INVENTION

In a first embodiment, the present invention provides a composition comprising melatonin encapsulated within a calcium alginate hydrogel.

In a second embodiment, the present invention provides an orally administrable dosage form comprising a composition according to the first embodiment held within a gel, wherein the gel is formed using starch as a gelling agent.

In a third embodiment, the present invention provides a process for the preparation of a composition comprising melatonin encapsulated within a calcium alginate hydrogel.

In a fourth embodiment, the present invention provides a process for the preparation of one or more orally administrable dosage forms comprising a composition according to the first embodiment held within a gel, wherein the gel is formed using starch as a gelling agent.

In a fifth embodiment, the present invention provides a composition according to the first embodiment, or an orally administrable dosage form according to the second embodiment, for use in the treatment of a sleep disorder.

In a sixth embodiment, the present invention provides for the use of a composition according to the first embodiment in the manufacture of a medicament, such as an orally administrable dosage form according to the second embodiment, for the treatment of a sleep disorder.

In a seventh embodiment, the present invention provides a method of treating a sleep disorder in an individual in need thereof, comprising administering a composition according to the first embodiment, or administering an orally administrable dosage form according to the second embodiment, to said individual.

BRIEF DESCRIPTION OF THE DRAWINGS

Examples of the invention will now be described in detail with reference to the accompanying drawings, in which.

DETAILED DESCRIPTION OF THE EMBODIMENTS

Figure 1:
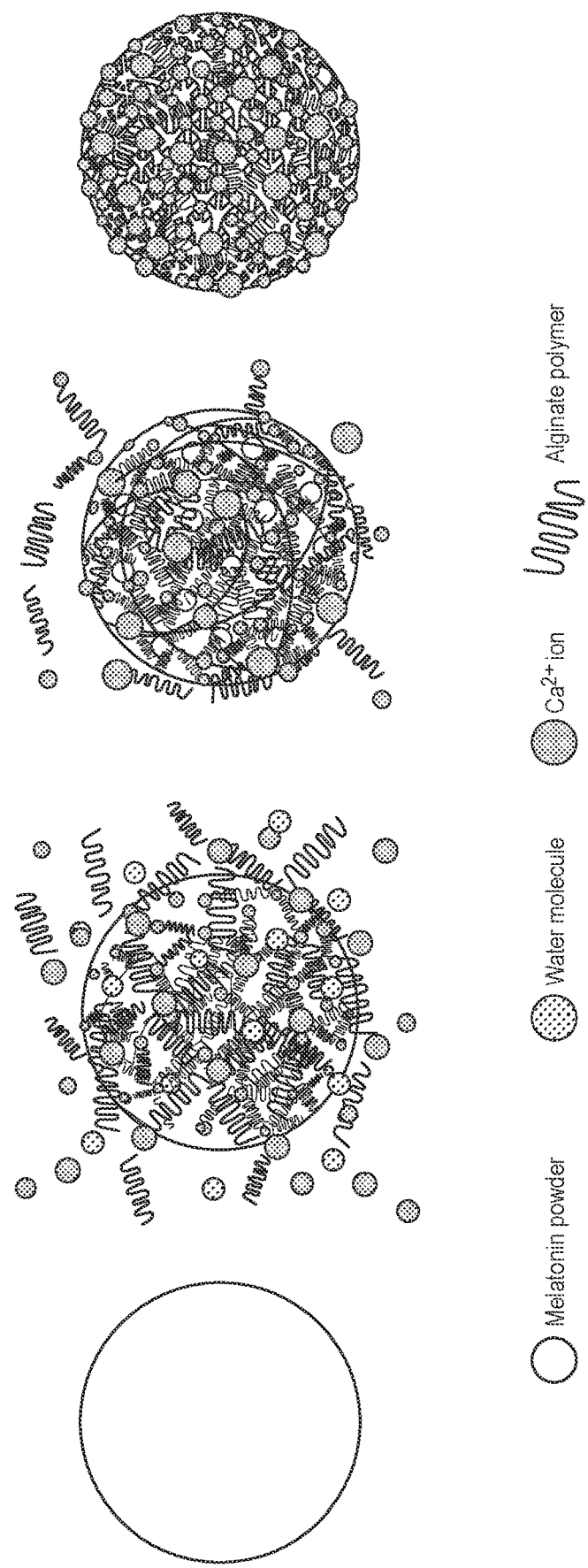
FIG. 1 shows a schematic representation of composition comprising melatonin encapsulated within a calcium alginate hydrogel.

In a first embodiment, the present invention provides a composition comprising melatonin encapsulated within a calcium alginate hydrogel. The inventors have discovered that such compositions provide sustained release of melatonin upon consumption and are also resistant to the harsh conditions used to manufacture gummy formulations, these being a preferred form of administration for this particular active ingredient. Preferably, the weight ratio of melatonin to calcium alginate hydrogel within the composition is from 5:95 to 15:85, more preferably about 10:90. The composition preferably comprises from 4 to 10 wt % water, more preferably from 6 to 8 wt % water, based on the total weight of the composition. The composition may further comprise sodium and lactate ions.

In a second embodiment, the present invention provides an orally administrable dosage form comprising a composition according to the first embodiment held within a gel, wherein the gel is formed using starch as a gelling agent. Gelatinised dosage forms are often referred to as gummy formulations and the inventors have discovered that the use of starch as the gelling agent is essential for the successful preparation of gummy formulations which use, as a sustained release component, a composition comprising melatonin encapsulated within a calcium alginate hydrogel.

Preferably, the dosage form comprises from 1 to 3 wt % of the composition according to the first embodiment based on the total weight of the dosage form. In a further preferred embodiment, the dosage form comprises melatonin which is not encapsulated within the calcium alginate hydrogel. This melatonin is included in order to provide an immediate release of active ingredient upon consumption, whilst the melatonin encapsulated within a calcium alginate hydrogel is included to provide a sustained release of active ingredient throughout the night. Preferably, the dosage form comprises from 0.01 to 0.03 wt % melatonin which is not encapsulated within the calcium alginate hydrogel, based on the total weight of the dosage form.

Whilst different forms of starch may be used, it is preferred that the gel is formed using potato starch as a gelling agent. A suitable commercially available potato starch is Perfectamyl Gel NF. Preferably, the final dosage form comprises from 7 to 17 wt % starch based on the total weight of the dosage form. Furthermore, the dosage form may comprise from 8 to 18 wt % water based on the total weight of the dosage form.

In a preferred embodiment, the dosage form further comprises one or more sweeteners, preferably in an amount of from 52 to 82 wt % based on the total weight of the dosage form. The one or more sweeteners are preferably selected from the group consisting of sucrose and corn syrup and are preferably sucrose, 53 to 73 DE corn syrup, and 32 to 52 DE corn syrup. In a more preferred embodiment, the dosage form comprises from 26 to 36 wt % sucrose, from 18 to 28 wt % 53 to 73 DE corn syrup and from 8 to 18 wt % 32 to 52 DE corn syrup, based on the total weight of the dosage form. The 53 to 73 DE corn syrup is preferably about 63 DE corn syrup (such as Globe 63 DE Corn Syrup). The 32 to 42 DE corn syrup is preferably about 42 DE corn syrup (such as Globe 42 DE Corn Syrup).

The dosage form preferably also comprises one or more acidulants, preferably in an amount of from 0.6 to 1.2 wt % based on the total weight of the dosage form. A preferred acidulant is citric acid. The dosage form preferably also comprises L-theanine, preferably in an amount of from 2 to 4 wt % based on the total weight of the dosage form. The dosage form preferably also comprises one or more natural flavours (for example natural blueberry flavour WONF (WS-320-249-8) and/or natural bitter masker binder flavour (TV-785-446-1)) and/or natural colours (for example fruit juice, such as grape juice, of which FruitMaxPurple 1302 WS is a commercially available example). The dosage form preferably also comprises a glazing agent (for example vegetable oil and/or carnuba wax, of which Capol 42-3073 A MB is a commercially available example).

The orally administrable dosage forms of the present invention provide sustained release of melatonin over an extended period of time and optionally also provide immediate release of melatonin. A combination of both immediate and sustained release of melatonin provides exposure throughout the night, providing more effective treatment of sleep disorders.

In a third embodiment, the present invention provides a process for the preparation of a composition comprising melatonin encapsulated within a calcium alginate hydrogel, said process comprising the following steps:
i) forming a preblend of melatonin, a source of calcium ions and a source of alginate;
ii) granulating the preblend by wet granulation to form granules of a composition comprising melatonin encapsulated within a calcium alginate hydrogel; and
iii) drying the granules to a water content less than 15 wt % based on the total weight of the granules.

Preferably, the source of calcium ions is calcium lactate and/or the source of alginate is sodium alginate. Preferably, the wet granulation step ii) comprises spraying water at a rate of from 500-1000 ml/min. Preferably the drying step iii) comprises drying the granules to a water content of from 6 to 8 wt % based on the total weight of the granules.

In a fourth embodiment, the present invention provides a process for the preparation of one or more orally administrable dosage forms comprising a composition comprising melatonin encapsulated within a calcium alginate hydrogel, said process comprising the following steps:
i) providing a mixture comprising starch and water;
ii) heating the mixture from step i) with high shear mixing to prepare the starch for gelatinization;
iii) cooling the mixture from step ii);
iv) combining the product of step iii) with a composition comprising melatonin encapsulated within a calcium alginate hydrogel;
v) transferring the product of step iv) into one or more moulds of a suitable size and shape for an orally administrable dosage form; and
vi) curing and drying the transferred product of step iv) to provide one or more orally administrable dosage forms comprising a composition (e.g., any composition disclosed herein) held within a gel.

Preferably, the mixture of step i) comprises starch and water in a weight ratio of from 35:65 to 55:45, preferably from 40:60 to 50:50, more preferably about 45:55. Preferably, the mixture of step i) further comprises one or more sweeteners. Preferably, the heating of step ii) is at a temperature of from 140 to 160° C. at a pressure of from 1 to 5 bar. Preferably, heating of step ii) is by direct steam injection. Preferably, during step iv), the product of step iii) is also combined with an acidulant and/or melatonin which is not encapsulated within a calcium alginate hydrogel and/or L-theanine and/or a natural flavour and/or a natural colour.

Preferably, the one or more products of step vi) are coated with a glazing agent.

As noted above, the therapeutic use of melatonin for the treatment of sleep disorders is well known. Accordingly, in a fifth embodiment, the present invention further provides a composition comprising melatonin encapsulated within a calcium alginate hydrogel, or an orally administrable dosage form comprising a composition comprising melatonin encapsulated within a calcium alginate hydrogel, for use in the treatment of a sleep disorder.

In a sixth embodiment, the present invention provides for the use of a composition according to the first embodiment in the manufacture of a medicament, such as an orally administrable dosage form according to the second embodiment, for the treatment of a sleep disorder.

In a seventh embodiment, the present invention provides a method of treating a sleep disorder in an individual in need thereof, comprising administering a composition according to the first embodiment, or administering an orally administrable dosage form according to the second embodiment, to said individual.

"Sustained release" melatonin is also known to the skilled artisan as slow release melatonin, continuous release melatonin, time release melatonin, prolonged release melatonin, and controlled release melatonin. The sustained release melatonin in the various embodiments disclosed herein is melatonin encapsulated within a calcium alginate hydrogel. "Immediate release" melatonin is also known to the skilled artisan as "quick release" melatonin, is optionally present in any of the embodiments disclosed herein, and is not encapsulated by calcium alginate hydrogel and preferably not encapsulated by any form of alginate.

In particularly preferred embodiments of the first through seventh embodiments noted above, oral administration of any of the orally administrable dosage forms disclosed herein provides all three of the following effects: (i) faster falling asleep (i.e., less delay to sleep), (ii) longer lasting sleep (i.e., more delay to waking from sleep), and (iii) enhanced relaxing, soothing and/or calming, all relative to an individual consuming a comparative product in which the melatonin and the optional L-Theanine are absent but otherwise is identically formulated.

In some embodiments, a single night-time dose of any of the orally administrable dosage forms disclosed herein is administered. In such embodiments, the single night-time dose may be administered in one distinct unit of the dosage form or a plurality of distinct units of the dosage form, preferably about thirty minutes before bedtime (e.g., 15-45 minutes before bedtime). As a particular non-limiting example, two units of the orally administrable dosage form (e.g., two gummies) may be administered as a serving comprising a predetermined amount of the melatonin, such as about 10 mg melatonin total/serving (e.g., 5-15 mg melatonin total/serving). Preferably the single night-time dose is administered to an individual (e.g., an individual with occasional sleeplessness) in a serving comprising (i) immediate release melatonin in an amount effective for the individual to fall asleep faster, (ii) time release melatonin in an amount effective for the individual to stay asleep longer, and (iii) optionally L-Theanine in an amount effective for at least one of relaxing, soothing or calming for the individual (e.g., about 100 mg L-Theanine/serving, such as 50-150 mg L-Theanine/serving).

In some embodiments, the orally administrable dosage form has one or more features selected from the group consisting of: suitable for Vegetarians, no Artificial Flavor, no Artificial Sweetener, no Milk, no Lactose, no Soy, no Gluten, no Wheat, no Fish, and no greater than 10 mg Sodium (e.g., no Sodium). Preferably the orally administrable dosage form has all of these features.

EXAMPLES

Example 1—Preparation of Sustained Release Melatonin Granulate

An example composition and method for the preparation of a sustained release melatonin granulate on industrial scale is given below:

Method

The raw materials calcium lactate, melatonin and sodium alginate were sieved on a net and combined in a slow rotation blender until homogenous. The resulting preblend was transferred into a fluid bed dryer, and the quantity of purified water indicated below was charged into a dissolutor. The melatonin granulate was then formed by the process of wet granulation, whereby the water was sprayed at a rate of from 500-2000 ml/min while shaking the preblend. A drying process was then performed by setting the inlet air temperature to within 60-80° C. to obtain a granulate with a water content within 6-8%. A cooling process was then performed by setting the inlet temperature to 20° C. in order to reach a temperature of the product less than 35° C.

Composition of Sustained Release Melatonin Preblend

| Ingredient | Unitary (mg) | Standard batch size (kg) |
| --- | --- | --- |
| Melatonin | 12.120 | 25.000 |
| Sodium alginate | 54.540 | 112.500 |
| Calcium lactate•5H$_2$O | 54.540 | 112.500 |
| Total | 121.200 | 250.000 |

Composition of Sustained Release Melatonin Granulate

| Ingredient | Unitary (mg) | Standard batch size (kg) |
| --- | --- | --- |
| Melatonin preblend | 121.200 | 250.000 |
| Purified water (evaporates upon drying) | 48.500 | 100.041 |
| Total | 121.200 | 250.000 |

Example 2—Preparation of Sustained Release Melatonin Gummy

An example composition and method for the preparation of a sustained release gummy on industrial scale is given below:

Method

A premix weigher was charged with pre-heated water (120° F., 153 lb) and potato starch (perfectamyl gel, 185 lb), and stirred at 50% mixing speed until homogenous. This was followed by the addition of 42 DE corn syrup (205 lb) and stirring was increased to 60% mixing speed until homogenous. Subsequently, 63 DE corn syrup (267 lb) was added and stirring was increased to 70% mixing speed until homogenous. Finally, granulated sugar (490 lb) was added and stirring was maintained at 70% mixing speed until homogenous.

The resulting premix slurry was then transported with vacuum to a buffer vessel, before pumping through a jet-cooker (149° C., back pressure of 3.5 bar). A pressure dissolver with direct steam injection and high shear mixing was used to open the starch granules for gelatinization.

Following the jet-cooker, the cooked mass is staged in a holding tank (190-210° F., pH=5.5-6.5) and then pumped back to the buffer vessel, which is used to quickly cool down the mass and reduce the water content via evaporation.

In a separate tank, cold water (3.3 lb) was combined with 63 DE corn syrup (9 lb) while stirring at 50% mixing speed for 45 seconds. This was followed by the addition of 50% w/w aqueous citric acid solution (2.7 lb), and stirred for a further 30 seconds at the same speed. Melatonin (3.03 lb) was then added and stirred for 60 seconds at 50% mixing speed. The sustained release melatonin granulate of Example 1 (0.03 lb) was added and stirred at 60% mixing speed for 2 to 3 minutes. Finally, L-threanine (4.68 lb) was added and stirred for 30 seconds at 60% mixing speed.

The cooked mass was then pumped to the additive blending system, where a portion thereof (124.34 lb) was mixed with the mix comprising melatonin (22.74 lb), natural blueberry flavour (1.13 lb), natural bitter masker (0.30 lb), and purple color mixture (1.50 lb).

After this final mixing step, the mass is transferred to depositor hoppers and dosed into starch filled trays for moulding into gummies (wet weight 3.75 g, pH 3.7-3.9). The gummies are then placed in a curing/drying room for 20-60 hours, at a temperature between 125-145° F. and 8-20% RH to achieve a dry gummy weight of 3.45 g. The gummies are then manually demoulded and coated with a glazing agent (Capol 42-3073 A MB).

Composition of Sustained Release Melatonin Gummy (Finished Product)

The dry gummy weight of the finished product is 3.45 g (range could be 2 g to 5 g).

| Ingredient | | | Wt % in cured gummy |
| --- | --- | --- | --- |
| Sucrose | Granulated sugar | Sweetener | 31.19 |
| 63 DE Corn syrup | Globe 63 DE Corn Syrup non-BE | Sweetener | 22.99 |
| Water | Water | Diluent | 13.33 |
| 41 DE Corn syrup | Globe 42 DE Corn Syrup Non-BE | Sweetener | 13.05 |
| Potato starch | Perfectamyl Gel NF | Gelling agent | 11.78 |
| L-Theanine | L-Theanine | Active ingredient | 3.11 |

-continued

| Ingredient | | | Wt % in cured gummy |
|---|---|---|---|
| Sustained release melatonin granulate | From Example 1 | Active ingredient | 2.01 |
| Citric acid | Citric Acid | Acidulant | 0.90 |
| Natural flavour | Natural Blueberry Flavor WONF (WS-320-249-8) (original) | Flavour | 0.75 |
| Natural colour | FruitMaxPurple 1302 WS | Colour | 0.50 |
| Natural flavour | Natural bitter masker (TV-785-446-1) | Flavour | 0.20 |
| Glazing agent | Capol 42-3073 A MB | Glazing agent | 0.18 |
| Immediate release melatonin | Melatonin | Active ingredient | 0.02 |

Example 3—Bioavailability Studies of Sustained Release Melatonin Gummy

Method

Three melatonin gummy formulations (which had been processed to replicate mastication) were subjected to in-vitro dissolution in simulated gastric media (0.1N HCl at 37° C.) in a modified analytical method based on the USP <2040> method. The formulations were the commercially available Natrol® 10 mg and NiteThru® products and a gummy formulation in accordance with the present invention (labelled as #1Sleep3 gummy (no botanicals)).

Results

Figure 2:
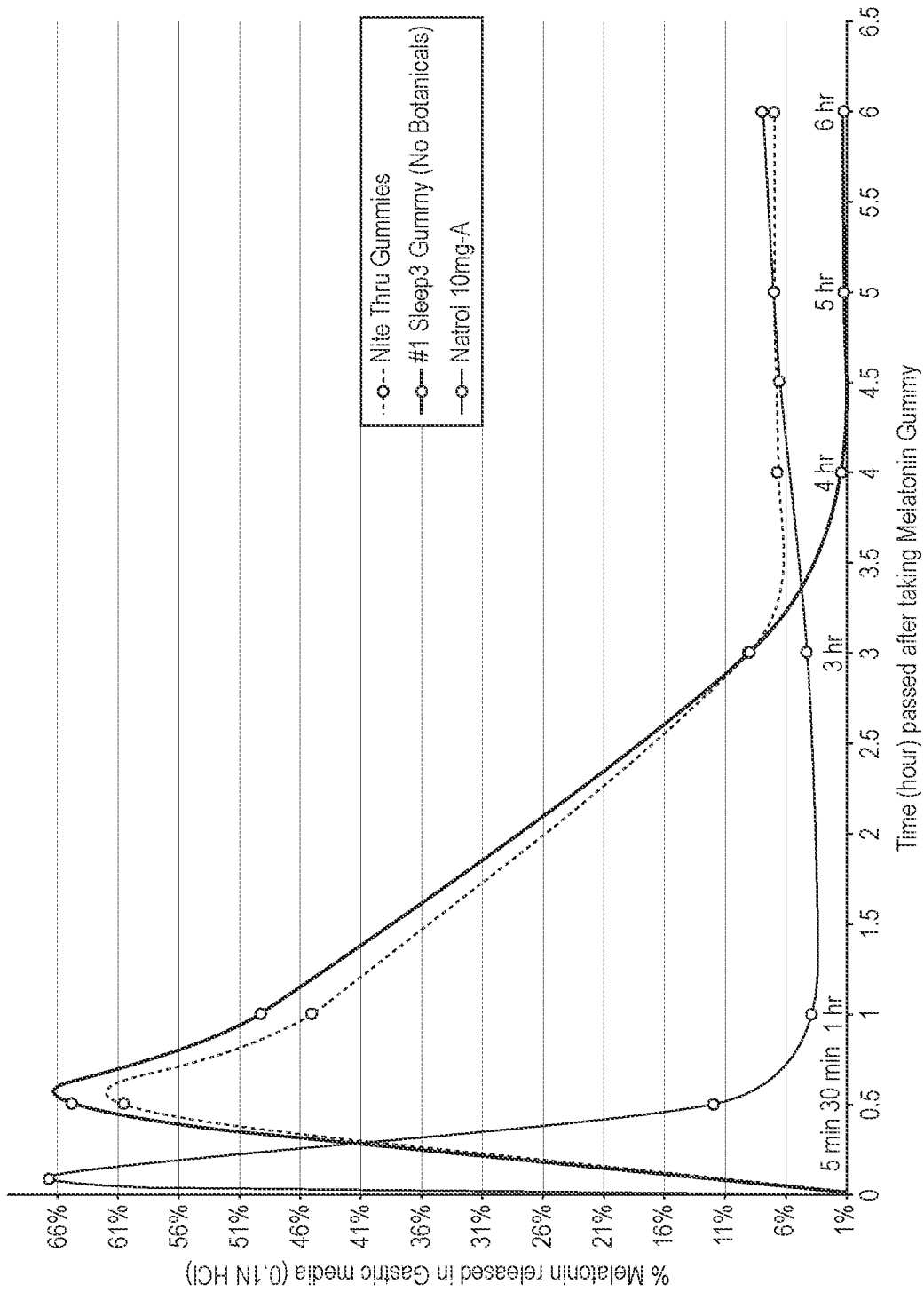
FIG. 2 shows the % melatonin released in gastric media over time for a composition of the present invention compared to the prior art Natrol® and NiteThru® products.

The melatonin dissolution profiles for these three formulations are shown in FIG. 2 below. It can be seen that the Natrol® 10 mg product provides rapid release of melatonin which is not sustained whereas the NiteThru® product and the formulation in accordance with the present invention provide a sustained release profile.

Example 4—Non-Limiting Example of Melatonin Gummy

| Supplement Facts Serving Size 2 Gummies Servings Per Container TBD | | |
|---|---|---|
| Amount Per Serving | | % Daily Value |
| Calories | 20 | |
| Total Carbohydrate | 5 G | 2%** |
| Total Sugars | 3 G | *** |
| Includes 3 g Added Sugars | | 6%** |
| Sodium | 10 Mg | <1% |
| Melatonin | 10 Mg | *** |
| L-Theanine | 100 Mg | *** |

**Percent Daily Values are based on a 2,000 calorie diet.
***Daily Value not established.

Other Ingredients: Glucose Syrup, Sugar, Modified Food Starch. Contains <2% of: Citric Acid, Natural Flavors, Fruit and Vegetable Juice (Color), Vegetable Oil (Contains Carnauba Wax).

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The invention claimed is:

1. An orally administrable dosage form comprising a composition comprising melatonin encapsulated within a calcium alginate hydrogel, wherein the composition is held within a gel, wherein the gel is formed using starch as a gelling agent, and wherein the weight ratio of the melatonin to the calcium alginate hydrogel is from 5:95 to 15:85, the dosage form further comprising additional melatonin which is not encapsulated within the calcium alginate hydrogel.

2. The dosage form according to claim 1, comprising from 1 to 3 wt % of the composition based on total weight of the dosage form.

3. The dosage form according to claim 1, comprising from 0.01 to 0.03 wt % of the additional melatonin which is not encapsulated within the calcium alginate hydrogel, based on total weight of the dosage form.

4. The dosage form according to claim 1, wherein the starch in the gelling agent comprises potato starch.

5. The dosage form according to claim 1, comprising from 7 to 17 wt % of the starch based on total weight of the dosage form.

6. The dosage form according to claim 1, comprising from 8 to 18 wt % water based on total weight of the dosage form.

7. The dosage form according to claim 1, further comprising one or more sweeteners.

8. The dosage form according to claim 7, comprising from 52 to 82 wt % of the one or more sweeteners based on total weight of the dosage form.

9. The dosage form according to claim 7, wherein the one or more sweeteners are selected from the group consisting of sucrose and corn syrup.

10. The dosage form according to claim 9, wherein the one or more sweeteners comprises sucrose, 53 to 73 DE corn syrup, and 32 to 52 DE corn syrup.

11. The dosage form according to claim 10, comprising from 26 to 36 wt % of the sucrose, from 18 to 28 wt % of the 53 to 73 DE corn syrup and from 8 to 18 wt % of the 32 to 52 DE corn syrup, based on total weight of the dosage form.

12. The dosage form according to claim 1, further comprising one or more acidulants.

13. The dosage form according to claim 12, comprising from 0.6 to 1.2 wt % of the one or more acidulants based on total weight of the dosage form.

14. The dosage form according to claim 12, wherein the one or more acidulants comprise citric acid.

15. The dosage form according to claim 1, further comprising L-theanine.

16. The dosage form according to claim 15, comprising from 2 to 4 wt % of the L-theanine based on total weight of the dosage form.

17. The dosage form according to claim 1, further comprising one or more natural flavours and/or natural colours.

18. The dosage form according to claim 1, further comprising a glazing agent.

\* \* \* \* \*